United States Patent [19]

Steer

[11] Patent Number: 4,775,373
[45] Date of Patent: Oct. 4, 1988

[54] OSTOMY APPLIANCE

[75] Inventor: Peter L. Steer, Surrey, England

[73] Assignee: E. R. Squibb and Sons, Inc., Princeton, N.J.

[21] Appl. No.: 5,297

[22] Filed: Jan. 20, 1987

Related U.S. Application Data

[63] Continuation of Ser. No. 758,920, Jul. 25, 1985, abandoned.

[30] Foreign Application Priority Data

Aug. 20, 1984 [GB] United Kingdom ............... 8421099

[51] Int. Cl.⁴ .............................................. A61F 5/44
[52] U.S. Cl. .................................... 604/338; 604/339
[58] Field of Search ........................ 604/277, 332–345; 285/331, DIG. 22; 24/535; 220/306, 307; 383/42, 43, 44, 45

[56] References Cited

U.S. PATENT DOCUMENTS

| | | | |
|---|---|---|---|
| 2,869,548 | 1/1959 | Mason | 604/340 |
| 3,520,301 | 7/1970 | Fenton | 604/338 |
| 3,588,149 | 6/1971 | Demler et al. | 285/331 |
| 3,759,415 | 9/1973 | Cloyd | 220/306 |
| 4,232,672 | 11/1980 | Steer et al. | 604/338 |
| 4,359,051 | 11/1982 | Oczkowski | 604/339 |
| 4,419,100 | 12/1983 | Alexander | 604/339 |
| 4,460,363 | 7/1984 | Steer et al. | 604/336 |
| 4,518,389 | 5/1985 | Steer et al. | 604/339 |

FOREIGN PATENT DOCUMENTS

| | | | |
|---|---|---|---|
| 0077392 | 4/1954 | Denmark | 604/333 |
| 2121902 | 1/1984 | United Kingdom | 604/332 |

Primary Examiner—C. Fred Rosenbaum
Assistant Examiner—Mario Costantino
Attorney, Agent, or Firm—Lawrence S. Levinson; Robert E. Lee, Jr.

[57] ABSTRACT

The ostomy appliance has two interengaging coupling elements. One of the elements is an annular plate which includes an engaging member formed by two ribs which diverge from each other to define a V-formation. One of the ribs has a stepped formation on its distal region. The other coupling element has an annular channel having cooperating formation adapted to engage the stepped formation, thereby connecting the coupling elements.

4 Claims, 2 Drawing Sheets

OSTOMY APPLIANCE

This is a continuation of co-pending application Ser. No. 758,920 filed on July 25, 1985 now abandoned.

BACKGROUND OF THE INVENTION

The present invention relates to an ostomy appliance.

Ostomy appliances are used by patients who have undergone abdominal surgery as a result of which an abdominal opening or stoma has been left in the body.

Such surgical techniques are well known, and, by way of example, reference is made to colostomy operations (in which the large intestine is brought through the abdominal wall) and illeostomy operations (in which the large intestine is completely removed and the samll intestine is brought through the abdominal wall). In each case, drainage or discharge from the digestive system of the patient takes place through the opening or stoma in the abdominal wall, and it is necessary to provide means to receive this drainage or discharge from the stoma, as it cannot be controlled by the patient.

One very successful commercially available arrangement is that known as the "Sur-Fit" or "System 2" which is commercially available from E. R. Squibb & Sons, Inc. That device has a first and second coupling element which connects to an ostomy bag or a pad of dressing on the patient. Reference may be made to U.S. Pat. No. 4,460,363 entitled OSTOMY BAG which issued to Peter L. Steer and John V. Edwards on July 17, 1984.

While the above described coupling system has been successful, it would be desirable to improve it by simplifying the shape of the body side coupling element so that it can be manufactured using a simple molding tool. Also, it has been found that some users find that the force needed to attach and detach the two coupling elements is larger than can conveniently be applied.

For patients whose discharge is of a slurry-like nature, difficulties have sometimes been encountered in that the crannies and recesses often present in an ostomy appliance which includes interengaging coupling elements become filled with discharged waste material. This makes the task of changing a bag by uncoupling the old bag and coupling on a new bag an unpleasant one, especially for old or less dexterous persons.

SUMMARY OF THE INVENTION

According to the present invention, in an ostomy appliance having interengaging coupling elements, one coupling element is formed by an annular plate defining a stomal orifice, the plate having projecting from a flat surface thereof an engaging member formed by two ribs which diverge from each other in a direction away from the plate, the ribs being made of a resilient flexible plastic and at least one of them having on its distal region a stepped formation intended for engagement with a cooperating formation on the bag side coupling element.

With such an arrangement, the two coupling elements can be pushed together or pulled apart using only moderate force, such as can easily be applied manually by an elderly or infirm person.

According to a preferred and highly advantageous embodiment of the invention, the face plate carries an annular chute located radially inwardly of the engaging member. This chute serves to prevent waste material from becoming lodged in recesses defined by the coupling elements when interengaged, or at least to greatly reduce the chance of this occurring.

The chute member may be of substantially cylindrical shape and, as stated, is molded integrally with one coupling element. Alternatively, however, the chute member may be a separate molding. It may be attached to the face plate by a plastic welding procedure, and for this purpose it may have a flat outwardly-extending flange. Heat welding or ultrasonic welding may be employed. As yet another alternative, the chute member may be omitted.

DETAILED DESCRIPTION OF THE PREFERRED EMBODIMENT

Figure 1:
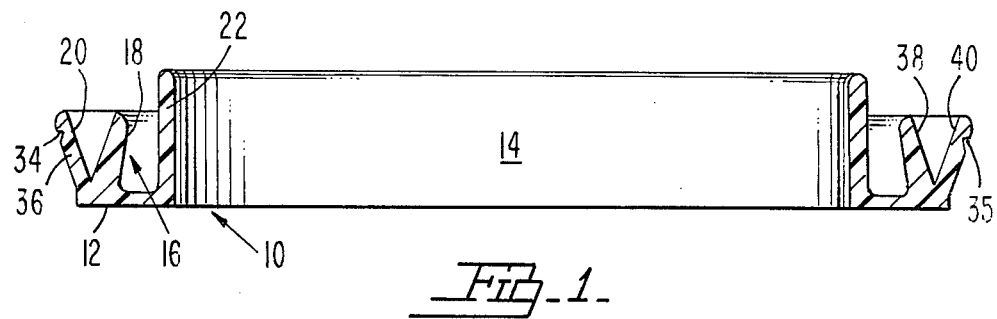
FIG. 1 is a central axial cross-section through one example of annular chute member according to the invention.
Figure 2:
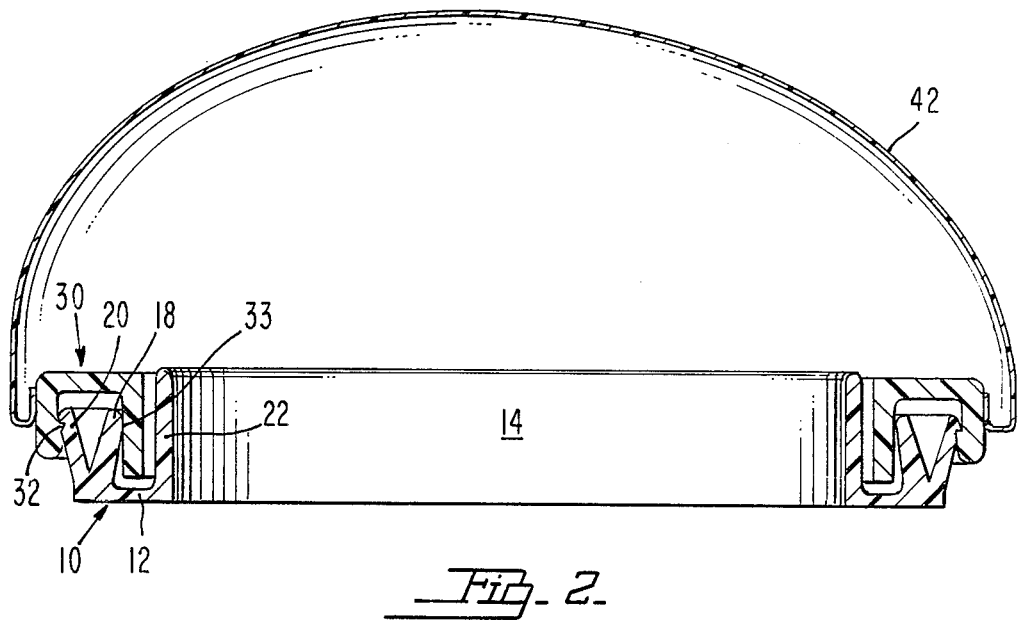
FIG. 2 is a like cross-section through a coupling showing the chute member of FIG. 1 in its operative position.

Referring now to FIGS. 1 and 2, the illustrated body side coupling element 10 comprises a face plate 12 having a central circular stomal orifice 14 therein. The plate 12 is made in one piece with an engaging member 16 formed by two diverging ribs 18 and 20. These are joined adjacent to the face plate 12 and diverge in a direction away from the face plate 12. As shown in cross-section, the ribs 18, 20 define a V-formation which encircles the stomal orifice 14.

Radially within the ribs 18, 20, and also encircling the stomal orifice is a chute 22. The purpose of the chute 22 is to conduct discharged waste directly into the interior of an ostomy bag 42, and to prevent such waste from becoming lodged in recesses or crevices in the interengaged coupling elements 10, 30, as shown in FIG. 2. However, the presence of the chute 22 is not essential to the present invention, and it is to be regarded as an optional improvement.

FIG. 2 illustrates the body side coupling element 10 interengaged with a bag side coupling element 30 attached to an ostomy bag 42 As shown, an internal rim 32 on the element 30 snaps over the rib 20 and is received in a recess 35 defined by a stepped formation comprising flat surfaces 34 and 36. These maintain the coupling elements 10, 30 securely connected together, but, due to the small radial overlap and the inherent flexibility of the plastic used, the coupling elements 10, 30 may easily be manually separated, even by elderly or infirm persons.

In a particular embodiment of the invention, the angle between the surfaces 38 and 40 of the respective ribs may be about 40 degrees, the axial length of the surface 36 may be about 0.010 inch (0.25 mm) and the radial extent of the surface 34 may be about 0.008 to 0.0084 inch (0.203 to 0.213 mm) and preferably should not be less than about 0.008 inch.

The preferred plastic for the coupling element 10 is low density polyethylene and this may have a Shore A hardness which is conventional in couplings of the kind shown in U.S. Pat. No. 4,460,363 entitled OSTOMY BAG which issued to Peter L. Steer and John V. Edwards on July 17, 1984.

A bag side coupling element 30, for example in accordance with the element 56 illustrated in U.S. Pat. No. 4,460,363 entitled OSTOMY BAG which issued to Peter L. Steer and John V. Edwards on July 17, 1984, cooperates with the body side coupling element 10 and when assembled, the inner wall of the rib 18 is engaged by a wall 33 of the element 30 thereby helping to insure that discharged waste material will be kept away from the inter-engaging parts of the two coupling elements 10, 30.

Figure 3:
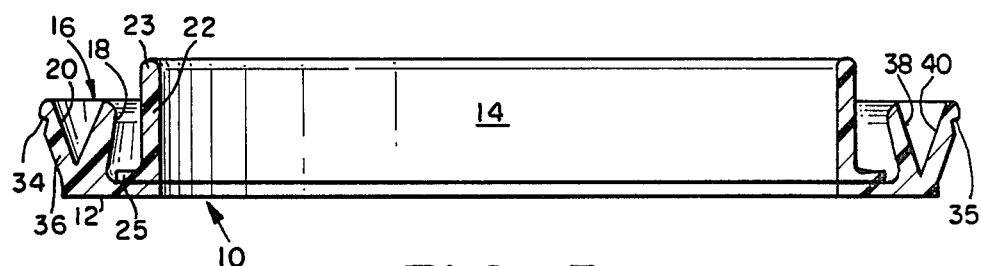
FIG. 3 is a cross-section through coupling member of an alternative embodiment.

While a particular embodiment of the invention has been particularly described and illustrated, it will be understood that modifications may be made without departing from the invention. Moreover, while the chute 22 has been illustrated as cylindrical, it may be tapered outwardly or inwardly if desired referring to FIG. 3, an alternative embodiment of the body side coupling element 10, of FIG. 1, is shown. In the embodiment of FIG. 3, the chute 22 is constructed of a piece 23 which is separate from the plate 12 which is attached to the plate 12 by welding a fast portion 25 to the plate 12.

I claim:

1. An ostomy appliance comprising:
   (a) a first coupling element comprising an annular plate defining a stomal orifice, said annular plate having projecting from a flat surface thereof an engaging member comprised of a pair of ribs each of said ribs extending away from the surface of said annular plate, one of said ribs being directed and biased outwardly with respect to said stomal orifice and the other one of said ribs being directed and biased inwardly toward said stomal orifice, said inwardly directed and biased rib being surrounded by said outwardly directed and biased rib, said ribs having their greatest separation from one another at their end which is most remote from said annular plate, said ribs encircling the stomal orifice, said ribs being made of a resilient, flexible plastic, and at least one of said ribs having a stepped formation encircling said rib adjacent its extremity remote from said annular plate; and
   (b) a second coupling element including an annular channel having radially inner and outer walls, said outer latter wall being provided with a cooperating formation which is engageable with said stepped formation, said pair of ribs adapted to fit within said annular channel and sealingly engage the inner and outer walls thereof.

2. The ostomy appliance of claim 1 in which said annular plate includes an annular chute located radially inwardly of the engaging member, said annular chute serving to substantially prevent waste material from becoming lodged in recessed defined by the coupling elements when interengaged.

3. The ostomy appliance of claim 2 in which said chute member is substantially cylindrical shape and is an integral part of said first coupling element.

4. The ostomy appliance of claim 2 in which said chute member is comprised of a separate molding which is attachable to said face plate and which includes a flat outwardly-extending flange, whereby it can be attached to the face plate by a plastic welding procedure.

* * * * *